United States Patent [19]
Buckley et al.

[11] Patent Number: 5,545,618
[45] Date of Patent: Aug. 13, 1996

[54] GLP-1 ANALOGS USEFUL FOR DIABETES TREATMENT

[76] Inventors: Douglas I. Buckley, 215 Brookward Rd., Woodside, Calif. 94062; Joel F. Habener, 217 Plymouth Rd., Newton Highlands, Mass. 02161; Joanne B. Mallory, 199 Acalanes, Apt. 3, Sunnyvale, Calif. 94086; Svetlana Mojsov, 504 E. 63rd St., New York, N.Y. 10021

[21] Appl. No.: 165,516

[22] Filed: Dec. 10, 1993

Related U.S. Application Data

[63] Continuation of Ser. No. 762,768, Sep. 20, 1991, which is a continuation-in-part of Ser. No. 468,736, Jan. 24, 1990, abandoned.

[51] Int. Cl.$^6$ .................... A61K 38/26; C07K 14/605
[52] U.S. Cl. ................................ 514/12; 530/324
[58] Field of Search ................. 514/12; 530/324

[56] References Cited

U.S. PATENT DOCUMENTS

| | | | |
|---|---|---|---|
| 4,221,777 | 9/1980 | Nishino | 424/12 |
| 4,598,065 | 7/1986 | Lundt et al. | 514/12 |
| 5,118,666 | 6/1992 | Habener | 514/12 |
| 5,120,712 | 6/1992 | Habener | 514/12 |

FOREIGN PATENT DOCUMENTS

| | | | |
|---|---|---|---|
| WO87/06941 | 11/1987 | WIPO | C07K 7/10 |

OTHER PUBLICATIONS

Mojsov et al., *J. Clin. Invest.* (1987) 79:616–619.
Holst et al., *FEBS Letters* (1987) 211(2):169–174.
Orskov et al., *Endocrinol.* (1988) 123(4):2009–2013.
Suzuki et al., *Diabetes Research and Clinical Practice* XIII Congress of the International Diabetes Federation, (1988) 5(Suppl. 1):S30 (abstract No. ORA–007–007).
Kreymann et al., *Lancet* (Dec. 5, 1987)pp. 1300–1303.
McDonald et al., *J. Biol. Chem.* (1969) 244:6199–6208.
Frohman et al., *J. Clin. Invest.* (1986) 78:906–913.
Murphy et al., *Peptide Res.* (1988) 1:36–41.
Hendrick et al., *Endocrine Society Program and Abstracts*, 70th Annual Meeting, Jun. 8–11, 1988, New Orleans, Louisiana, p. 182, (abstract No. 648).
Yanaihara et al., *Glucagon and Related Peptides*, Satellite Symposium of 8th International Congress of Endocrinology, Jul. 15–16, 1988, Osaka, Japan, p. 10, (lecture No. 4).
Gefel et al., *Endocrinol.* (1990) 126(4):2164–2168.
Larner et al., Eds., *Methods in Diabetes Research* (vol. 1 Part C: Laboratory Methods) John Wiley & Son's, New York, New York, pp. 291–307.
Schmidt et al., *Diabetologia* (1985) Springer–Verlag, pp. 704–707.
Sutton et al., *Transplantation* (1986) 42(6):689–691.
Stewart et al., *Solid Phase Synthesis*, Second Edition, (1984) p. 25.
Suzuki et al., *Endocrinol.* (1989) 125(6):3109–3114.
Smith et al., *Principles of Biochemistry*, Seventh Edition, (1983) pp. 32–33.

*Primary Examiner*—Christine M. Nucker
*Assistant Examiner*—Benet Prickril
*Attorney, Agent, or Firm*—Morrison & Foerster

[57] ABSTRACT

The invention provides effective analogs of the active GLP-1 peptides, 7-34, 7-35, 7-36, and 7-37, which have improved characteristics for treatment of diabetes Type II. These analogs have amino acid substitutions at positions 7-10 and/or are truncated at the C-terminus and/or contain various other amino acid substitutions in the basic peptide. The analogs may either have an enhanced capacity to stimulate insulin production as compared to glucagon or may exhibit enhanced stability in plasma as compared to GLP-1 (7-37) or both. Either of these properties will enhance the potency of the analog as a therapeutic. Analogs having D-amino acid substitutions in the 7 and 8 positions and/or N-alkylated or N-acylated amino acids in the 7 position are particularly resistant to degradation in vivo.

14 Claims, 6 Drawing Sheets

| | | | |
|---|---|---|---|
| A-1 | (H†)⁷ | A-11 | (M†)⁷ |
| A-2 | (Y)⁷ | A-12 | (N-formyl-H)⁷ |
| A-3 | (Y†)⁷ | A-13 | (N-formyl-H†)⁷ |
| A-4 | (F)⁷ | A-14 | (N-acetyl-H)⁷ |
| A-5 | (F†)⁷ | A-15 | (N-acetyl-H†)⁷ |
| A-6 | (R)⁷ | A-16 | (N-isopropyl-H)⁷ |
| A-7 | (R†)⁷ | A-17 | (N-isopropyl-H†)⁷ |
| A-8 | (Orn)⁷ | A-18 | (K)⁷ |
| A-9 | (Orn†)⁷ | A-19 | (K†)⁷ |
| A-10 | (M)⁷ | A-20 | (N-acetyl-K)⁷ |
| | | | |
| A-21 | (M)⁷ | A-31 | (beta-Ala⁸) |
| A-22 | (P)⁷ | A-32 | (Aib⁸) |
| A-23 | (P†)⁷ | A-33 | (E†)⁹ |
| A-24 | (A†)⁸ | A-34 | (D)⁹ |
| A-25 | (Sar)⁸ | A-35 | (D†)⁹ |
| A-26 | (C)⁸ | A-36 | (Cya)⁹ |
| A-27 | (C†)⁸ | A-37 | (T)⁹ |
| A-28 | (G)⁸ | A-38 | (T†)⁹ |
| A-29 | (S)⁸ | A-39 | (N)⁹ |
| A-30 | (S†)⁸ | A-40 | (N†)⁹ |
| | | | |
| A-41 | (Q)⁹ | A-51 | (T†)¹⁰ |
| A-42 | (Q†)⁹ | A-52 | (N)¹⁰ |
| A-43 | (Cit)⁹ | A-53 | (N†)¹⁰ |
| A-44 | (MSO)⁹ | A-54 | (Q)¹⁰ |
| A-45 | (Acetyl-K)⁹ | A-55 | (Q†)¹⁰ |
| A-46 | (S)¹⁰ | A-56 | (Cit)¹⁰ |
| A-47 | (S†)¹⁰ | A-57 | (MSO)¹⁰ |
| A-48 | (Y)¹⁰ | A-58 | (Acetl-K)¹⁰ |
| A-49 | (Y†)¹⁰ | A-59 | (F†)¹⁰ |
| A-50 | (T)¹⁰ | A-60 | (S)²²(R)²³(R)²⁴(Q)²⁶ |

FIG. 2A

| | | | |
|---|---|---|---|
| A-61 | (S)$^8$(Q)$^9$(Y)$^{16}$(K)$^{18}$(D)$^{21}$ | A-71 | (A)$^{25}$ |
| A-62 | (T)$^{16}$ (K)$^{18}$ | A-72 | (Q)$^{26}$ |
| A-63 | (Y)$^{16}$ | A-73 | (K$^\dagger$)$^{26}$ |
| | | A-74 | (G)$^{26}$ |
| A-65 | (E)$^{15}$ | A-75 | (S)$^{26}$ |
| A-66 | (K)$^{18}$ | A-76 | (A)$^{26}$ |
| A-67 | (D)$^{21}$ | A-77 | (L)$^{26}$ |
| A-68 | (S)$^{22}$ | A-78 | (I)$^{26}$ |
| A-69 | (R)$^{23}$ | A-79 | (R$^\dagger$)$^{26}$ |
| A-70 | (R)$^{24}$ | A-80 | (M)$^{26}$ |
| | | | |
| A-81 | (K$^\dagger$)$^{34}$ | A-91 | (L)$^{31}$ |
| A-82 | (G)$^{34}$ | A-92 | (I)$^{31}$ |
| A-83 | (S)$^{34}$ | A-93 | (A)$^{31}$ |
| A-84 | (A)$^{34}$ | A-94 | (Y)$^{31}$ |
| A-85 | (L)$^{34}$ | A-95 | (R$^\dagger$)$^{34}$ |
| A-86 | (I)$^{34}$ | A-96 | (Q)$^{36}$ |
| A-87 | (Q)$^{34}$ | A-97 | (K)$^{36}$ |
| A-88 | (M)$^{34}$ | A-98 | (K$^\dagger$)$^{36}$ |
| A-89 | (F)$^{31}$ | A-99 | (G)$^{36}$ |
| A-90 | (V)$^{31}$ | A-100 | (L)$^{36}$ |
| | | A-101 | (I)$^{36}$ |
| | | A-102 | (Q)$^{36}$ |
| | | A-103 | (M)$^{36}$ |
| | | A-104 | (R$^\dagger$)$^{36}$ |
| | | A-105 | (S)$^{36}$ |
| | | A-106 | (A)$^{36}$ |

FIG. 2B

GLP-1 ANALOGS USEFUL FOR DIABETES TREATMENT

This application is a continuation of application Ser. No. 07/762,768, filed Sep. 20, 1991, which is a continuation-in-part of U.S. application Ser. No. 07/468,736, filed 24 Jan. 1990, now abandoned.

TECHNICAL FIELD

The invention relates to the field of improved pharmaceutical compositions. Specifically, the invention concerns analogs of the glucagon-like peptide I fragment 7-36 or 7-37 with improved pharmacological properties.

BACKGROUND ART

Glucose metabolism is regulated by a number of peptide hormones, including insulin, glucagon, and gastric inhibitory peptide (GIP). The complex mechanism by which these peptide hormones regulate this metabolism and the manner in which they affect each other is at least partially elucidated. For example, glucagon binds to receptors on the surface of the pancreatic beta cells which produce insulin, and stimulates insulin secretion. Glucagon-like peptide I has been suggested to stimulate insulin secretion but this has not been confirmed.

Several of these hormones originate from a mammalian glucagon precursor "proglucagon" which is a 180 amino acid peptide. Proteolysis and processing of this peptide results in a number of these protein hormones; the results of the processing depend on the origin of the cells in which this occurs. For example, in the pig and rat pancreas, proglucagon is processed to form glucagon and glicentin-related pancreatic peptide, a large peptide which contains both GLP-1 and GLP-2 sequences. In porcine small intestine, the secreted products are the 69 amino acid glucagon-containing peptide glicentin and the two glucagon-like sequences, GLP-1 and GLP-2 as separate peptides.

In any event, however, the overall sequence of proglucagon contains the 29-amino acid sequence of glucagon, the 36 or 37 amino acid sequence of GLP-1 and the 34 amino acid sequence of GLP-2, separated by amino acid spacer sequences.

Early attempts to assign a pattern of activity to GLP-1 gave ambiguous results, and it was subsequently concluded that truncated forms of this peptide are biologically active. Mojsov, S., et al. *J Clin Invest* (1987) 79:616–619 disclose that only the 31 amino acid peptide GLP-1(7-37) strongly stimulates the release of insulin from pancreas; although both the truncated and full length 37 amino acid form had earlier been found in pancreas and intestine. It has been demonstrated that GLP-1(7-36), possibly with the carboxy terminus amidated, is also a potent mediator of insulin release. (See, e.g., Holst, J. J., et al. *FEBS Letters* (1987) 211:169–174).

inhibition of glucagon secretion and to circulating half-life. The physiological effects of the truncated forms in potentiating glucose-induced insulin secretion have been shown as described above by Holst, J. J., et al. and Mojsov, S., et al. (supra). The activity of the truncated hormones in inhibiting glucagon release has been shown by Orskov, C., et al. *Endocrinol* (1988) 123:2009–2013; Suzuki, S., et al. *Diabetes Research: Clinical Practice* (1988) 5(Supp. 1):S30. The circulating half-life of these truncated forms is short—approximately four minutes as shown by Kreymann et al. *The Lancet* (Dec. 5, 1987) 1300–1303. The modified forms of these truncated GLP-1 peptides provide the opportunity to optimize these properties.

There is some literature relating to the study of degradation of peptide hormones in the liver and in plasma and the half-life of such hormones in vivo generally. An early paper by McDonald, J. K. et al., *J Biol Chem* (1969) 244:6199–6208 showed that a dipeptidase was responsible for the degradation of glucagon in rat liver. Studies on the growth hormone releasing factor, a member of the general glucagon, GLP-1, GLP-2 family, was shown to be rapidly degraded in plasma in vitro and also in vivo by a dipeptidase, (Frohman, L. A. et al., *J Clin Invest* (1986) 78:906–913). Murphy, W. A. et al., in *Peptide Research* (1988) 1:36–41, showed that some but not all alkylated growth hormone releasing factor peptides had higher potency in vivo. In particular, for example, the triisopropylated GRF-29 was found to be 106 times more active than GRF-29 itself. On the other hand, GRF-29 which was in methylated at the N-terminus was only 40% as potent as the parent. It was also shown that substitution of D-Ala position 2 of this hormone enhanced its potency. It was, of course, not certain to what effect on properties the enhancement of potency could be attributed.

Others have attempted some modifications of GLP-1(7-37). It has been shown that deletion of the histidine residue at position 7 greatly diminishes the activity of the hormone (Suzuki, S., et al. (supra); Hendrick, G. K., et al. *Abstract: Endocrine Society Meeting, New Orleans, La.* (1988)). There have been conflicting reports concerning the effect of one or more C-terminal deletions (Suzuki, S., et al. (supra); Yanaihara, C., et al. *Abstract for A Glucagon and Related Peptides Satellite Symposium*, 8th International Congress of Endocrinology, Jul. 15–16, 1988, Osaka, Japan). However, there is an extensive literature with regard to modifications of other members of this peptide hormone family, such as GIP, glucagon releasing factor (GRF), secretin and vasoactive intestinal peptide (VIP).

DISCLOSURE OF THE INVENTION

The invention provides modified forms of the GLP-1(7-34); (7-35); (7-36) or (7-37) human peptide or the C-terminal amidated forms thereof. The native peptides have the amino acid sequence:

```
7          10              15              20              25
H—A—E—G—T—F—T—S—D—V—S—S—Y—L—E—G—Q—A—A—

30                  37
K—E—F—I—A—W—L—V—K—(G)—(R)—(G)
```

The invention described below concerns analogs of these truncated forms of GLP-1, which have desirable combinations of characteristics as they relate to potency in potentiating glucose-induced insulin secretion and glucose-induced wherein (G), (R), and (G) are present or absent depending on indicated chain length. The modified forms contain one or more alterations of the native structure and are of improved ability for therapeutic use. Either the modified forms have greater potency than glucagon to potentiate insulin secretion or enhanced stability in plasma or both. This potency and enhanced stability can be assessed as described below.

The standard one letter abbreviation code for amino acids is used.

The analogs of the invention which show enhanced insulin stimulating properties have the foregoing sequence, or the C-terminal amide thereof, with at least one modification selected from the group consisting of:

(a) substitution of a neutral amino acid, arginine, or a D form of lysine for lysine at position 26 and/or 34 and/or a neutral amino acid, lysine, or a D form of arginine for arginine at position 36;

(b) substitution of an oxidation-resistant amino acid for tryptophan at position 31;

(c) substitution according to at least one of:
Y for V at position 16;
K for S at position 18;
D for E at position 21;
S for G at position 22;
R for Q at position 23;
R for A at position 24; and
Q for K at position 26;

(d) a substitution comprising at least one of:
an alternative small neutral amino acid for A at position 8;
an alternative acidic amino acid or neutral amino acid for E at position 9;
an alternative neutral amino acid for G at position 10; and
an alternative acidic amino acid for D at position 15; and (e) substitution of an alternative neutral amino acid or the D or N-acylated or alkylated form of histidine for histidine at position 7.

With respect to modifications (a), (b), (d) and (e), the substituted amino acids may be in the D form, as indicated by a superscript †, e.g., C†. The amino acids substituted at position 7 can also be in the N-acylated or N-alkylated forms.

Thus, one aspect of the invention is directed to peptides having enhanced insulin stimulating properties analogous to the above-mentioned truncated forms of GLP-1( 7-34) to GLP-1(7-37), as described above.

In another aspect, the invention is directed to peptides which show enhanced degradation resistance in plasma as compared to GLP-1(7-37) wherein this enhanced resistance to degradation is defined as set forth below. In these analogs, any of the above-mentioned truncated forms of GLP-1(7-34) to GLP-1(7-37) or their C-terminal amidated forms is modified by (a) substitution of a D-neutral or D-acidic amino acid for H at position 7, or (b) substitution of a D-amino acid for A at position 8, or (c) both, or (d) substitution of an N-acylated or N-alkylated form of any naturally occurring amino acid for H at position 7.

Thus, analogs of the invention which are resistant to degradation include (N-acyl (1-6C) AA)$^7$ GLP-1(7-37) and (N-alkyl (1-6C) AA)$^7$ GLP-1(7-37) wherein when AA is a lysyl residue, one or both nitrogens may be alkylated or acylated. AA symbolizes any amino acid consistent with retention of insulin stimulating activity.

For substitutions of D-amino acids in the 7 and 8 positions, the D residue of any acidic or neutral amino acid can be used at position 7 and of any amino acid at position 8, again consistent with insulin stimulating activity. Either or both of position 7 and 8 can be substituted by a D-amino acid; the D-amino acid at position 7 can also be acylated or alkylated as set forth above. These modified forms are applicable not only to GLP-1(7-37) but also the shorter truncated analogs as set forth above.

In other aspects, the invention is directed to pharmaceutical compositions containing one or more of these peptides as active ingredients and to methods to treat Type II diabetes using these peptides or compositions thereof.

BRIEF DESCRIPTION OF THE DRAWINGS

FIG. 2 gives a list of various compounds of the invention.

MODES OF CARRYING OUT THE INVENTION

Figure 1:
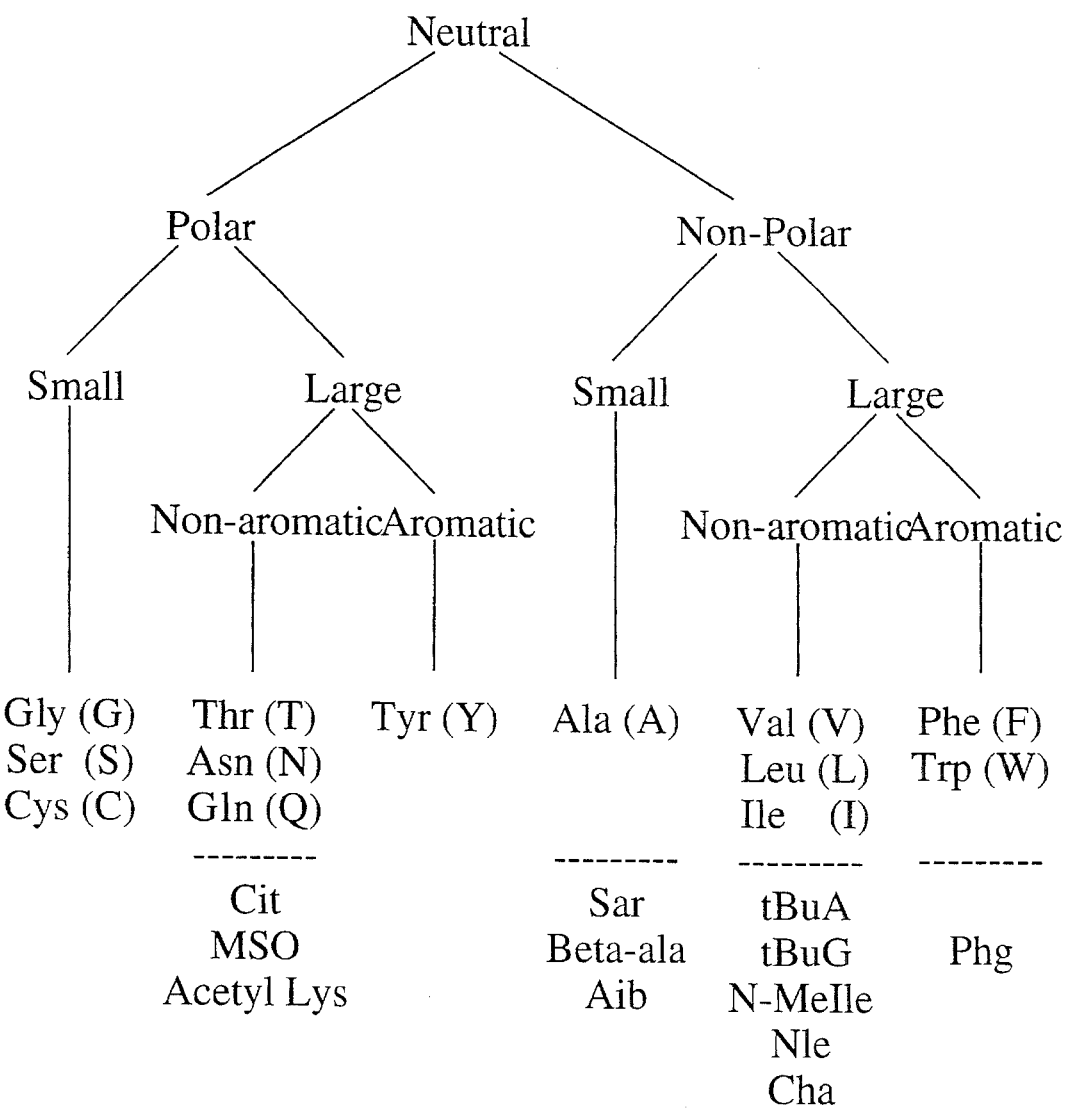
FIG. 1 schematically outlines the classification of amino acids as used herein.

The analogs of the invention, which are modified forms of the GLP-1(7-34), (7-35), (7-36) or (7-37) are characterized by showing greater potency than glucagon in an in vitro assay measuring insulin release from isolated rat islets in culture, or by enhanced stability in plasma or both.

ASSAYS FOR ANALOGS WITH ENHANCED INSULIN RELEASE

Stimulating Properties

One group of analogs of the invention is more potent than glucagon in stimulating insulin release from islet cells. By being "more potent than glucagon in stimulating insulin release from islet cells" is meant that the analog referred to shows greater potency in an in vitro assay selected from the group consisting of the following: Rat islets for these assays are isolated by the method of Sutton, R. et al., *Transplantation* (1986) 42:689–691, incorporated herein by reference. Briefly, Sprague-Dawley male rats are anesthetized and the lower end of the common bile duct is cannulated with a 2 FG cannula tied in place. The left and right hepatic ducts are then ligated separately above the region of the entry of pancreatic ducts into the biliary tree. The rats are killed by exsanguination and 3 mL Hank's solution containing 7.5 mM CaCl$_2$, 20 mM HEPES buffer and 1–6 mg/mL Type I collagenase are run into the cannula to uniformly distend the pancreas. The pancreas is then excised and placed in a beaker on ice prior to incubation in Hank's solution containing 20 mM HEPES buffer at 37° C.

After 13–25 min of incubation, the pancreas is removed and placed in Hank's solution containing 5 g/l bovine serum albumin and 20 mM HEPES buffer at 4° C. All of the pancreatic tissue is then gently syringed through a 14 FG needle, suspended in further Hank's solution containing HEPES as above, centrifuged at 50 g for 10 sec and the supernatant is discarded. The tissue pellet is resuspended and again gently syringed, followed by another wash, after which the dispersed tissue is passed through a nylon mesh filter of 500 u pore size. The filtered tissue is centrifuged at 350 g for 5 sec, the supernatant discarded, and the tissue is then suspended in 25% Ficoll made up in Hank's with HEPES as above, on which was layered a discontinuous density gradient of 23%, 20%, and 11% Ficoll solutions.

This density gradient was spun at 750 g for 10 min at 4° C., and the tissue obtained from the upper two interfaces was washed three times in Hank's solution and viewed through a dissecting microscope for hand picking of islets.

In one approach the ability of the GLP-1 analog to potentiate secretion from these Islets is then determined according to the method of Schatz, H. et al., in "Methods in Diabetes Research" (1984) Volume 1, Part C: pages 291–307, incorporated herein by reference. In this method, 5–10 islets per test tube are incubated in 1 mL Krebs-Ringer-bicarbonate buffer (KRB buffer). For testing, glucagon or the modified analog of the invention is added at 5–10 µg/mL. The level of insulin released may be measured by the method of Jensen, S. L. et al., *M J Physiol* (1978) 235:E381–E386, incorporated herein by reference.

The following protocol is a preferred method to measure stimulation of insulin secretion. After collagenase digestion, the islets are allowed to recover overnight by incubation in DMEM (Dulbecco's Modified Eagle Medium 16 w/o glucose), 2.8 mM glucose, 10% fetal bovine serum (FBS) at 37° C., 5% $CO_2$.

The next day, islets to be used for the experiment are transferred to DMEM, no glucose, 0.2% BSA (Armour, clinical grade, made at 5% stock) for a 60 min preincubation in serum-free, glucose-free medium. Islets are picked up by Eppendorf pipette and transferred to 60 mm TC plates containing 8.0 mL medium and returned to the incubator for 60 min. Islets are counted during this transfer. (Note: each data point is 5 islets, experiments are usually performed in quadruplicate; therefore, 20 islets are used per data point.) Typically, recoveries are 150–200 islets per pancreas. Any suspect islets—too ragged or falling apart—are not used.

During the 60 min preincubation, the experiment is set up, so that all that is needed at the end of the preincubation is to transfer islets in groups of 5 to experimental conditions. The experiment is set up in 48 well TC plates with 0.5 mL medium per well. To DMEM-0.2% BSA is added glucose to desired concentration (usually 2.8 mM for hypoglycemic conditions, 5.6 mM glucose for euglycemic, or 16.7 mM glucose for hyperglycemic) and test compound at various dose ranges (typically, 1 pM to 100 nM). Test compound is diluted from stock stored at −80° C. and at −0.3 mM serially into phosphate buffered saline (PBS) 0.2% BSA to prevent loss on sides of tubes. After medium plus test compound is mixed, 0.5 mL each is added to 4 wells for quadruplicate data points.

After the preincubation period, 5 islets are added per well. Islets are picked up-by eppendorf pipette in 25 ul volume. Incubation continues another 60 min, at which time 0.3 mL is harvested per well with care taken not to pick up islets. Wells are then rechecked for islet number. Medium is then assayed for insulin content using an insulin RIA. If medium is not immediately assayed, it is stored at −20° C. until assay. Dose response curves for insulin secretion are plotted and $ED_{50}$ is calculated from the curves.

Higher potency as compared to glucagon is defined as either higher levels of insulin released by the analog using the same concentrations of glucagon and analog or, alternatively, the same level of insulin release but using a lower concentration of analog than glucagon.

While the foregoing assays form specific criteria for judging enhanced potency, alternative assays can also be used as substitutes for those set forth above.

An additional test for potency of the compounds of the invention measures their ability to stimulate cAMP production in RIN 1046-38 cells. This assay can be conducted as follows:

On day 1, $5 \times 10^5$ RIN 1046-38 cells (Drucker, D. J., et al., *Proc Natl Acad Sci USA* (1987) 84:3434–3438) are seeded into individual wells of 6-well dishes with 2.5 mL M199 culture medium. On day 4, cells are re-fed with fresh medium and on day 5 the assay is performed. At this time there are ~$2.0–2.5 \times 10^6$ cells per well. Assays are only performed on cell passage $\leq 24$.

At time −60 min, monolayers are washed twice with 2.5 mL PBS, and medium is changed to 1.0 mL of DMEM medium plus 4.5 g/l glucose and 0.1% BSA (assay medium). At 0 time, medium is aspirated and fresh assay medium, 1.0 mL, containing test compound is added. Test compound is added in 50 ul volume of PBS plus 0.1% BSA; controls are added in vehicle alone. Incubation is continued for 0 to 60 min.

At termination, conditioned medium and monolayer are harvested to measure both extra- and intracellular cAMP content. For extracellular measurement, medium is removed and centrifuged to remove any cellular debris. For intracellular determination, after medium removal, 1.0 mL of ice cold 95% ethanol is added to monolayer. Cells are collected by scraping, lysed by two cycles of quick freeze/thawing using liquid $N_2$, and cell debris then removed by centrifugation. Aliquots (1/40th well content) of conditioned medium and ethanol cell extract are measured in duplicate for cAMP levels using an RIA kit by the acetylated protocol.

As above, higher potency as compared to glucagon is defined either as higher cAMP stimulation by both the analog and glucagon at the same concentration, or the same cAMP stimulation by the analog at a lower concentration.

Still other assays for measurement of enhanced potency to mediate insulin release can be used.

The ability of the compounds to potentiate the release of insulin can be tested both in vitro and in vivo. Insulin released can be detected using a standard antibody assay both in analyzing plasma in in vivo studies and in analyzing media or perfusion liquid in vitro.

For example, a useful in vitro assay uses the pancreatic infusion assay method of Penhos, J. C., et al. *Diabetes* (1969) 18:733–738, as employed in the method of Weir, G. C., et al. *J Clin Investigat* (1974) 54:1403–1412. Insulin secretion can also be measured by the method described by Holst, J. J., et al. *FEBS Letters* (1987) 211:169–174 (supra). Also useful as an assay for insulinotropic effect is the measurement of stimulation of adenylate cyclase in the RIN 1046-38 cell line. Drucker, D. J. et al., *Proc Natl Acad Sci USA* (1987) 84:3434–3438 (supra).

Inhibition of glucagon release can be shown as described by Orstov, C., et al. *Endocrinol* (1988) 123:2009–2013; Suzuki, S., et al. *Diabetes Research: Clinical Practice* (1988) 5(Supp. 1):S30 (both supra).

ASSAYS FOR ENHANCED STABILITY TO DEGRADATION

The therapeutic efficiency of the GLP-1 analogs of the invention can also be enhanced by providing analogs with increased half-lives in vivo. By "enhanced half-life in vivo" is meant a demonstrated ability to resist degradation in the presence of plasma according to an assay selected from the group consisting of the following. In all assays, the plasma is prepared by collecting blood into heparinized tubes, placing the tubes on ice and centrifuging at about 3,000 rpm for 10 minutes in a tabletop centrifuge. The separated plasma is stored at 4° C.

A. Radiolabel Sequencing:

The GLP analog is labeled by radio-iodination in position 19 using standard radiolabeling methods. After exchange into RIA buffer (50 mM NaHPO$_4$ pH 7.4, 0.25% BSA (Armour insulin and FFA free), 0.5% BME, 0.002% polylysine (Sigma 15,000 mw), 0.05% Tween 20, 0.1% NAN$_3$), the radioiodinated peptide (about 10$^5$ cpm/50 mL) and cold uniodinated peptide (20 μl 100 nM) are added into 2 ml of plasma to a final concentration of i nM and incubated in a circulating water bath for preset times. Total RIA buffer added to plasma never exceeds 5% of total volume. At the end of incubation, 10% bacitracin (w/v) in water is added to a final concentration of 0.1% to stop the reaction.

The plasma is then extracted using C18 Sep-Pak to separate the analog and any fragments from the bulk of the plasma proteins. Sep-Pak cartridges (Waters) are washed with 2 mL of 1-propanol, followed by 2 mL of water and then equilibrated with 2 mL of 20% CH$_3$CN containing 0.1% trifluoroacetic acid (TFA) (Buffer A).

The bacitracin-treated plasma is made 20% CH$_3$CN with CH$_3$CN containing 0.1% TFA and is expressed slowly through a 3 mL plastic syringe through the cartridge. The cartridge is then washed with two 1 mL Buffer A washes and eluted with a single 2 mL wash of 50% CH$_3$CN containing 0.1% TFA (Buffer B) into a siliconized 12×75 glass tube. Recovery of the analog or fragments is more than 90%.

The eluates are concentrated to 100 μl in a Speed vac and transferred to a 1.5 mL Eppendorf tube to which a 1 mL RIA buffer rinse of the original tube had been added.

To purify any analog or its fragments when the analogs of GLP-1(7-37) are used, the concentrates are treated with 5 μl of antiserum prepared to a synthetic peptide corresponding to residues 24–37 which recognizes GLP-1, GLP-1(7-37) but not GLP-1(7-36). When the shorter forms of analogs aroused, alternate carboxy terminal-specific antisera (prepared in the same manner but using a peptide corresponding to residues 24–34, 24–35 or 24–36 as immunogen) are used. To this is added 100 μl of a 10% (w/v) solution of protein A-Sepharose (Pharmacia) in PBS, and the mixture is incubated overnight at 4° C. with gentle rocking. The Sepharose is then pelleted with a 5 second spin in an Eppendorf centrifuge at 4° C. after which the pellet is washed two times with cold RIA buffer and four times with cold PBS.

Polyclonal antisera were raised in New Zealand White rabbits against a synthetic peptide fragment corresponding to residues 24 to 37 of GLP-1(7-37) using the method of Mosjoy, S. et al., *J Biol Chem* (1986) 261:11880–11889. Initial immunizations were into the inguinal lymph nodes and used Freund's complete adjuvant. Two subcutaneous boosts were performed at 1 week intervals after the initial immunization and used Freund's incomplete adjuvant. For a single immunization or boost 100 μg peptide and 100 μg methylated BSA dissolved in 0.3 mL phosphate-buffered saline (PBS) were emulsified with 0.9 mL adjuvant. Bleeds (50 mL) began at week 6 after the initial immunization and continued at 1 month intervals thereafter. Repeat boosts were performed as above when titers dropped noticeably from the level of the previous bleed.

Serum was prepared by allowing the blood to clot overnight at 4° C. The clot was pelleted by centrifugation at 2000 g for 15 minutes and the serum removed. Serum is stored in aliquots at −20° or −80° C.

The peptides are then eluted from the antibody protein-A sepharose complex with three 100 μl washes of Buffer B. The combined 300 μl of wash are then applied directly to an ABI model 47TA sequencer used according to the manufacturer's instructions. Fractions from each cycle are then diverted for counting. Counting can be effected in 4 mL aqueous scintillant (ACS, Amersham).

The cycle at which label appears indicates the extent of degradation from the N-terminus. If no degradation from the N-terminus has occurred in the GLP-1(7-37) analog, all of the label will appear in the 13th cycle, corresponding to the tyrosine at position 19; if degradation has occurred, the label will appear in earlier cycles.

B. Assay by RP-HPLC:

While the foregoing method is a clear criterion for exhibiting a longer half-life in plasma, alternative forms of the assay for this property can also be used. In one convenient assay, the analog can be assessed for degradation into fragments using reverse phase-HPLC, since the fragments have different retention times from the analog per se. In this assay, the analog is added to plasma for various times and recovered similarly to the method described above for radiolabel sequencing analysis. Specifically, the analog at a concentration of 100 nM in RIA buffer is spiked into 1 mL plasma to a final concentration of 1 nM and after incubation in 37° C. circulating water bath for various preset times, the reaction is stopped by bringing the plasma to 0.1% (w/v) in bacitracin.

The peptides are then purified by Sep-Pak extraction as described above. The eluates are concentrated to about 1 mL on a Speed-vac, diluted with 1 mL distilled water, frozen at 80° C. and lyophilized overnight. The powder is resuspended in 0.5 mL Buffer C (0.1% TFA in water) per mL starting plasma and 0.25 mL are injected on a Hewlett-Packard 109OL liquid chromatograph using an Alltech C18 column (0.45×25 cm; 10 μm particle size) with a Brownlee 2 cm C18 guard column. The extraction is monitored at OD$_{214}$ throughout the run and the solvent flow rate was 1 mL/minute. A gradient between Buffer C and Buffer D (0.1% TFA in acetonitrile) is set up over a 40 minute run time. The gradient starts at 35% D is held for the first 2 minutes after injection and then increased to 42% D over 24 minutes. The gradient is then increased to 60% D over the next two minutes, held at this level for 2 minutes and returned to 35% D over the next 2 minutes. The % D remains at 35% for the remaining 8 minutes of the run. Fractions are collected at 0.5 minute intervals for the first 30 minutes of each run and dried in a Speed-vac. The samples can be assayed for the presence of analog or fragment using RIA (measuring competition with labeled GLP-1(7-37) for binding to C-terminal specific antiserum) or by any conventional or convenient alternative method.

Radioimmunoassays for the amino or carboxyl terminus of GLP-1(7-37) use a single antibody displacement format. Binding of $^{125}$I-GLP-1(7-37) to antibody is incrementally displaced by increasing concentrations of unlabeled peptide in solution. Antibody bound iodinated peptide is separated from free iodinated peptide in solution by precipitation of the antibody-peptide complex with Pansorbin™ (Boheringer Mannheim). The resulting pellet is then counted on a gamma counter.

C. Loss of Binding to N-Terminal Specific Antibodies:

A third approach to assessment of half-life in plasma utilizes polyclonal or monoclonal antibodies specifically prepared to the N-terminus which will fail to bind degraded analog. These antisera were raised against a synthetic peptide corresponding to GLP-1(7-22) which contains an additional cysteine residue at the carboxyl terminus and is specifically coupled to KLH via the cysteine using mal-sac-HSNA as described by Aldwin, L. et al. *Analytical Biochem*

(1987) 164:494–501. Polyclonal antibodies were generated in New Zealand white rabbits by giving a primary immunization into the inguinal lymph nodes of 500 μg conjugate emulsified with Freund's complete adjuvant and then two subsequent boosts of 200 μg each in Freund's incomplete adjuvant at 2 week intervals. Blood (50 mL) is collected monthly thereafter and boosts are performed if titers are low. For generation of monoclonal antibodies, Balb/c mice were immunized intraperitoneally with 200 μg of conjugate in 0.5 ml Freund's complete adjuvant. Mice were boosted biweekly with 100 μg conjugate in 0.5 ml Freund's incomplete adjuvant. Cells isolated from the spleens of these mice were fused with Fox-NY cells to produce monoclonal cell lines. Monoclonal secreting cell lines are produced using the standard Kohler-Millstein technology. Monoclonal supernatants and polyclonal sera are screened using an ELISA method for binding to GLP-1(7-37) but not to GLP-1(8-37). The specificity is confirmed in standard solution phase RIA.

The kinetics of degradation of GLP-1(7-37) are followed by adding the analog to human plasma in RIA buffer, generally 10 μL of 100×concentrated peptide is added to 1 mL of plasma to obtain the desired concentration; the sample is then incubated in 37° C. water bath and triplicate 50 μL aliquots are removed at various times. The aliquots are immediately ethanol precipitated for radioimmunoassay using a competition for binding of the N-terminal specific antibody with radioiodinated GLP-(1(7-37). Disappearance of the ability to compete with the radioiodinated GLP-1(7-37) peptide indicates degradation of the analog.

In any of these assays, the analog tested has enhanced stability if it is less rapidly degraded than GLP-1(7-37).

The Analogs

The analogs of the invention having higher potency than glucagon or having enhanced degradation resistance are modified forms of GLP-1(7-34) through GLP-1(7-37) wherein, in some instances, amino acids of certain classes are substituted for the naturally occurring residues.

Amino acid residues can be generally subclassified into four major subclasses as follows and as shown in FIG. 1.

Acidic: The residue has a negative charge due to loss of H ion at physiological pH and the residue is attracted by aqueous solution so as to seek the surface positions in the conformation of a peptide in which it is contained when the peptide is in aqueous medium at physiological pH.

Basic: The residue has a positive charge due to association with H ion at physiological pH and the residue is attracted by aqueous solution so as to seek the surface positions in the conformation of a peptide in which it is contained when the peptide is in aqueous medium at physiological pH.

Neutral/nonpolar: The residues are not charged at physiological pH and the residue is repelled by aqueous solution so as to seek the inner positions in the conformation of a peptide in which it is contained when the peptide is in aqueous medium. These residues are also designated "hydrophobic" herein.

Neutral/polar: The residues are not charged at physiological pH, but the residue is attracted by aqueous solution so as to seek the outer positions in the conformation of a peptide in which it is contained when the peptide is in aqueous medium.

It is understood, of course, that in a statistical collection of individual residue molecules some molecules will be charged, and some not, and there will be an attraction for or repulsion from an aqueous medium to a greater or lesser extent. To fit the definition of "charged", a significant percentage (at least approximately 25%) of the individual molecules are charged at physiological pH. The degree of attraction or repulsion required for classification as polar or nonpolar is arbitrary, and, therefore, amino acids specifically contemplated by the invention have been specifically classified as one or the other. Most amino acids not specifically named can be classified on the basis of known behavior.

Amino acid residues can be further subclassified as cyclic or noncyclic, and aromatic or nonaromatic, self-explanatory classifications with respect to the side chain substituent groups of the residues, and as small or large. The residue is considered small if it contains a total of 4 carbon atoms or less, inclusive of the carboxyl carbon. Small residues are, of course, always nonaromatic.

For the naturally occurring protein amino acids, subclassification according to the foregoing scheme is as follows (see also FIG. 1).

Acidic: Aspartic acid and Glutamic acid;
Basic/noncyclic: Arginine, Lysine;
Basic/cyclic: Histidine;
Neutral/polar/small: Glycine, Serine and Cysteine;
Neutral/polar/large/nonaromatic: Threonine, Asparagine, Glutamine;
Neutral/polar/large/aromatic: Tyrosine;
Neutral/nonpolar/Small: Alanine;
Neutral/nonpolar/large/nonaromatic: Valine, Isoleucine, Leucine, Methionine;
Neutral/nonpolar/large/aromatic: Phenylalanine, and Tryptophan.

The gene-encoded amino acid proline, although technically within the group neutral/nonpolar/large/cyclic and nonaromatic, is a special case due to its known effects on the secondary conformation of peptide chains, and is not, therefore, included in this specific defined group.

Certain commonly encountered amino acids, which are not encoded by the genetic code, include, for example, beta-alanine (beta-ala), or other omega-amino acids, such as 3-amino propionic, 4-amino butyric and so forth, alpha-aminoisobutyric acid (Aib), sarcosine (Sar), ornithine (Orn), citrulline (Cit), homoarginine (Har), t-butylalanine (t-BuA), t-butylglycine (t-BuG), N-methylisoleucine (N-MeIle), phenylglycine (Phg), and cyclohexylalanine (Cha), norleucine (Nle), cysteic acid (Cya) and methionine sulfoxide (MSO). These also fall conveniently into particular categories.

Based on the above definition,
Sar and beta-ala are neutral/nonpolar/small;
t-BuA, t-BuG, N-MeIle, Nle and Cha are neutral/nonpolar/large/nonaromatic;
Har and Orn are basic/noncyclic;
Cya is acidic;
Cit, Acetyl Lys, and MSO are neutral/polar/large/nonaromatic; and
Phg is neutral/nonpolar/large/aromatic.

See, also, FIG. 1.

The various omega-amino acids are classified according to size as neutral/nonpolar/small (beta-ala, i.e., 3-aminopropionic, 4-aminobutyric) or large (all others).

Other amino acid substitutions for those encoded in the gene can also be included in peptide compounds within the scope of the invention and can be classified within this general scheme.

The nomenclature used to describe GLP-1 analog compounds of the present invention follows the conventional practice wherein the amino group is assumed to the left and the carboxy group to the right of each amino acid in the peptide. In the formulas representing selected specific embodiments of the present invention, the amino- and carboxy-terminal groups, although often not specifically shown, will be understood to be in the form they would assume at physiological pH values, unless otherwise specified. Thus, the N-terminal $H^+_2$ and C-terminal-$O^-$ at physiological pH are understood to be present though not necessarily specified and shown, either in specific examples or in generic formulas.

The foregoing describes the status of the termini at neutral pH; it is understood, of course, that the acid addition salts or the basic salts of the peptides are also included within the scope of the invention. At high pH, basic salts of the C-terminus and carboxyl-containing side chains may be formed from nontoxic pharmaceutically acceptable bases, and suitable counter- ions include, for example, $N^+$, $K^+$, $Ca^{++}$ and the like. Suitable pharmaceutically acceptable nontoxic organic cations can also be used as counter ions. In addition, as set forth above, the peptides may be prepared as the corresponding amides.

Suitable acid addition salts with respect to the N-terminus or amino group-containing side chains include the salts formed from inorganic acids such as hydrochloric, sulfuric, or phosphoric acid and those formed from organic acids such as acetic, citric, or other pharmaceutically acceptable non-toxic acids.

In the peptides shown, each encoded residue where appropriate is represented by a single letter designation, corresponding to the trivial name of the amino acid, in accordance with the following conventional list:

| Amino Acid | One-Letter Symbol |
| --- | --- |
| Alanine | A |
| Arginine | R |
| Asparagine | N |
| Aspartic acid | D |
| Cysteine | C |
| Glutamine | Q |
| Glutamic acid | E |
| Glycine | G |
| Histidine | H |
| Isoleucine | I |
| Leucine | L |
| Lysine | K |
| Methionine | M |
| Phenylalanine | F |
| Proline | P |
| Serine | S |
| Threonine | T |
| Tryptophan | W |
| Tyrosine | Y |
| Valine | V |

The amino acids not encoded genetically are abbreviated as indicated above.

In the specific peptides of the present application, the L-form of any amino acid residue having an optical isomer is intended unless otherwise expressly indicated by a dagger (†) superscript. While the residues in the analogs of the invention peptides are normally in the natural L optical isomer form, one or two, preferably one, amino acid in addition to a specified "same-amino-acid-D form," substitution for the naturally occurring amino acid may be in the D configuration.

In the notation used in designating specific analogs, the positions modified are shown as superscripts to the replacement amino acid; thus, $(H^†)7$-GLP-1(7-37) is the noted GLP-1(7-37) form with the D form of histidine substituted at position 7; $(S)^{22}(R)^{23}(R)^{24}(Q)^{26}$-GLP-1(7-37) refers to the 7-37 GLP form with serine at position 22, arginine at positions 23 and 24, and glutamine at position 26.

PREFERRED EMBODIMENTS

A. Enhanced Stimulatory Analogs

For analogs with increased insulin-stimulating activity, particularly preferred analog compositions of the invention are those wherein only limited numbers of modifications or substitutions, as compared to GLP-1 truncated forms are made. Thus, preferred are those analogs where the modifications described in only one or two of the paragraphs (a)-(e) set forth above in the Disclosure section occurs.

Thus, among the preferred analogs of the invention are those wherein the (7-34), (7-35), (7-36) or (7-37) form of GLP-1 has been modified only by substitution of a neutral amino acid, arginine, or a D form of lysine for lysine at position 26 and/or 34 and/or a neutral amino acid, lysine, or a D form of arginine for arginine at position 36 (paragraph (a)). Particularly preferred are those wherein the amino acid substituted for lysine at positions 26 and 34 is selected from the group consisting of $K^†$, G, S, A, L, I, Q, R, $R^†$ and M, and for arginine at position 36 is selected from the group of K, $K^†$, G, S, A, L, I, Q, M, and $R^†$.

Also preferred are analogs wherein the sole modification is the substitution of an oxidation-resistant amino acid for tryptophan at position 31 (paragraph (b)). Particularly favored substitutions are selected from the group consisting of F, V, L, I, A, and Y.

Also preferred are those analogs wherein the only modification is at least one of those specific substitutions set forth in paragraph (c). Particularly preferred are those analogs wherein combined substitutions of S for G at position 22, R at positions 23 and 24 for Q and A respectively, and Q for K at position 26 have been made, or substitutions of Y for V at position 16 and K for S at position 18 have been made, or these substitutions plus D for E at positions 21 have been made.

Also preferred are analogs wherein the sole modifications are those set forth in paragraph (d). Particularly preferred among these are those wherein the small neutral amino acid substituted for alanine at position 8 is selected from the group consisting of S, $S^†$, G C, $C^†$, Sar, $A^†$, beta-ala and Aib; and/or the acidic or neutral amino acid substituted for glutamic acid at position 9 is selected from the group consisting of $E^†$, D, $D^†$, Cya T, $T^†$, N, $N^†$, Q, $Q^†$, Cit, MSO, and acetyl-K; and/or the alternative neutral amino acid substituted for glycine at position 10 is selected from the group consisting of S, $S^†$, Y, $Y^†$, T, $T^†$, N, $N^†$, Q, $Q^†$, Cit, MSO, acetyl-K, F, and $F^†$; and/or wherein D is substituted for E at position 15.

Also preferred are analogs wherein position 7 alone has been altered (paragraph (e)). Preferred substitutions are those wherein the amino acid substituted for histidine at position 7 is selected from the group consisting of $H^†$, Y, $Y^†$, F, $F^†$, R, $R^†$, Orn, $Orn^†$, M, $M^†$, N-formyl-H, N-formyl-$H^†$, N-acetyl-H, N-acetyl-$H^†$, N-isopropyl-H, N-isopropyl-$H^†$, N-acetyl-K; N-acetyl-$K^†$, P and $P^†$.

Also preferred are embodiments with a combination of only two of the above-referenced classes of modified forms, in addition to the following specific embodiments.

The following specific analogs are preferred:

$(H^†)^7$-GLP-1(7-37);

$(Y)^7$-GLP-1(7-37);

$(N\text{-acetyl-}H)^7$-GLP-1(7-37);

$(N\text{-isopropyl-}H)^7$-GLP-1(7-37);

$(A^†)^8$-GLP-1(7-37);

$(E^†)^9$-GLP-1(7-37);

(D)⁹-GLP-1(7-37);
(D⁺)⁹-GLP-1(7-37);
(F⁺)¹⁰-GLP-1(7-37)
(S)²²(R)²³(R)²⁴(Q)²⁶-GLP-1(7-37); and
(S)⁸(Q)⁹(Y)¹⁶(K)¹⁸(D)²¹-GLP-1(7-37).

B. Enhanced Stability Analogs

Preferred forms of analogs with enhanced stability also have only one, or at most two, amino acid modifications.

Preferred substitutions for the histidine at position 7 include the D-forms of acidic or neutral amino acids or the D-forms of histidines. Preferred are P⁺, D⁺, E⁺, N⁺, Q⁺, L⁺, V⁺, I⁺and H⁺.

The histidine at position 7, or a replacement (D or L), can also be N-alkylated (1-6C) or N-acylated (1-6C). Alkyl groups are straight or branched chain (including cyclic) hydrocarbyl residues of the indicated member of C. Acyl groups are of the formula RCO—wherein R is alkyl as defined above. Preferred alkyl groups are t-propyl, α-propyl and ethyl; preferred acyl are acetyl and propionyl. Preferred residues which may be alkylated or acylated include P, D, E, N, Q, V, L, I, K and H in either the D or L form.

Preferred substitutions for alanine at position 8 are the D-forms of P, V, L, I and A; also preferred are the D-forms of D, E, N, Q, K, T, S and H.

It is understood, as is demonstrated below, that some specific analogs show both enhanced insulin release stimulating activity and enhanced stability.

Preparation

The analogs of the invention can be prepared using standard solid-phase techniques for the synthesis of peptides. As is generally known, peptides of the requisite length can be prepared using commercially available equipment and reagents following the manufacturers' instructions for blocking interfering groups, protecting the amino acid to be reacted, coupling, deprotection, and capping of unreacted residues. Suitable equipment can be obtained, for example, from Applied BioSystems in Foster City, Calif., or Biosearch Corporation in San Raphael, Calif.

In a preferred method, the peptides are synthesized using standard automated solid-phase synthesis protocols employing t-butoxycarbonyl-alpha-amino acids with appropriate side-chain protection. Completed peptide is removed from the solid phase support with simultaneous side-chain deprotection using the standard hydrogen fluoride method. Crude peptides are further purified by semi-preparative reverse phase-HPLC (Vydac $C_{18}$) using acetonitrile gradients in 0.1% trifluoroacetic acid (TFA). The peptides are vacuum dried to remove acetonitrile and lyophilized from a solution of 0.1% TFA in water. Purity is verified by analytical RP-HPLC. The peptides can be lyophilized and then solubilized in either water or 0.01M acetic acid at concentrations of 1–2 mg/mL by weight.

The use of the aforementioned synthetic methods is needed if nonencoded amino acids or the D forms of amino acids occur in the peptides. However, for peptides which are gene-encoded, recourse can also be had to recombinant techniques using readily Synthesized DNA sequences in commercially available expression systems.

Formulation and Administration

The analogs of the invention are useful in the treatment of Type II diabetes. The analogs can be administered systemically in a variety of formulations, as is generally known in the art. Formulations appropriate for particular modes of administration for peptides are set forth in, for example, *Remington's Pharmaceutical Sciences,* latest edition, Mack Publishing Company, Easton, Pa. In general, the formulations utilize an effective amount of the analog or mixtures of analogs and at least one pharmaceutically acceptable excipient.

A variety of modes of administration are effective in systemic treatment, such as injection, including intravenous, intramuscular, subcutaneous, and intraperitoneal injection; transmembrane or transdermal administration, using suitable suppositories or sprays; and, if properly formulated, oral administration. Suitable excipients for injection include various physiological buffers, such as Hank's solution and Ringer's solution; suitable transmembrane or transdermal formulations contain penetrants such as bile salts or fusidates; and typical oral formulations contain protective agents which inhibit the digestion of the active ingredient. Also available are various slow-release formulations involving macromolecular matrices such as pyrrolidones and methylcellulose. Alternate drug delivery systems include liposomes and microemulsions. A variety of formulations are workable, and the provision of appropriate formulations for the selected peptides and administration routes is generally understood by practitioners.

A typical dosage range for the compounds of the invention is about 1 pg/kg-1 mg/kg body weight, although these are approximations depending upon a large number of factors including the potency of the analog, its circulating half-life, the individual characteristics of the subject, and the like. Optimization of administration of insulin for diabetic treatment of individuals is well established, and similar optimization protocols are employed here.

EXAMPLES

The following examples are intended to illustrate, but not to limit, the invention.

Example 1

Enhanced Insulin Stimulation by Analogs of the Invention

As shown in FIG. 2, analogs of the invention having a variety of substituents modifying the native structure have been prepared. Some of these analogs have been tested in the adenylate cyclase assay referenced above, with the results shown in Table 1.

TABLE 1

|  | ED50 nM Duplicate Assays | |
| --- | --- | --- |
| Positive Controls | | |
| GLP-1(7-37) | 0.16 | 0.25 |
| GLP-1(7-36)(amide) | 0.16 | 0.20 |
| Related Peptides | | |
| Glucagon | 80.0 | 140 |
| Secretin | NR | — |
| GIP | 10.0 | 37.5 |
| GRF | NR | — |
| Negative Controls | | |
| GLP-1(1-37) | >1000 | 2900 |
| GLP-1(2-37) | — | — |
| GLP-1(3-37) | 70 | 81 |
| GLP-1(4-37) | 130 | 200 |
| GLP-1(5-37) | 150 | 750–970 |
| Analogs | | |
| (H⁺)⁷-GLP-1(7-37) | 1.1 | 2.2 |
| (Y)⁷-GLP-1(7-37) | 5.0 | 5.0 |
| (N-acetyl-H)⁷-GLP-1(7-37) | 15.5 | — |
| (N-isopropyl-H)⁷GLP-1(7-37) | 15.5 | — |
| (K)⁷-GLP-1(7-37) | 350.0 | — |
| (A⁺)⁸-GLP-1(7-37) | 0.40 | 0.55 |

TABLE 1-continued

| | ED50 nM Duplicate Assays | |
|---|---|---|
| $(E^+)^9$-GLP-1(7-37) | 55.0 | 74.0 |
| $(D)^9$-GLP-1(7-37) | 0.17 | 0.28 |
| $(D^+)^9$-GLP-1(7-37) | 0.90 | 0.90 |
| $(F^+)^{10}$-GLP-1(7-37) | 12.0 | 23.0 |
| $(S)^{22}(R)^{23}(R)^{24}(Q)^{26}$-GLP-1(7-37) | 0.94 | 1.8 |
| $(S)^8(Q)^9(Y)^{16}(K)^{18}(D)^{21}$-GLP-1(7-37) | 0.31 | — |

The various analogs of the invention thus show a useful range of potencies in the insulinotropic assay.

Example 2

Enhanced Stability of GLP-1 Analogs

A. Demonstration of Mode of Inactivation

The GLP-1(7-37) truncated hormone was radioiodinated and the purified peptide was incubated with plasma and assayed by radiolabel sequencing as described hereinabove. The sequencing was done on samples at time zero, 15 minutes and 60 minutes. At time zero, a single peak of radioactivity was found at cycle 13 indicating no degradation. After 15 minutes, the amount of radioactivity in cycle 13 was reduced, and that in cycle 11 was enhanced. After 60 minutes of incubation, virtually all of the counts appeared at cycle 11.

It thus appears that a single dipeptidyl aminopeptidase cleavage is responsible for the degradation of the GLP-1(7-37) peptide.

The foregoing results are consistent with degradation as measured by RIA using N-terminal specific and C-terminal specific antisera. When incubated with plasma as described above and tested by RIA, no diminution in the ability of the recovered fragment to inhibit binding of radiolabeled GLP-1(7-37) to carboxy terminal-specific antibody was found; however, the ability to inhibit binding to the amino terminal-specific antibody decreased almost to zero after 1 hour.

B. GLP-1(7-37) Analogs Tested by Radiolabel Sequencing

Figure 3A:
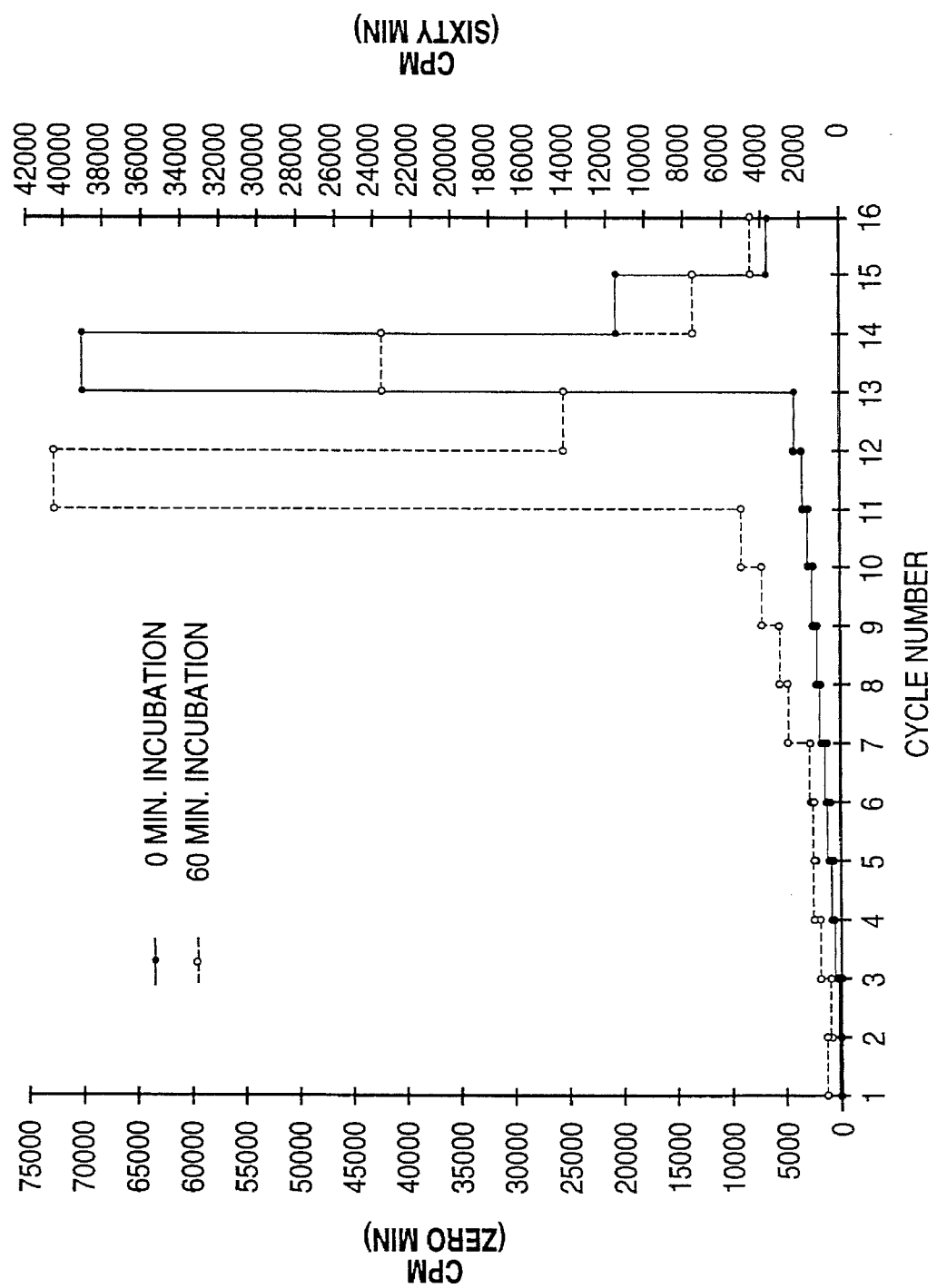
FIG. 3 shows the results of radiolabel sequencing analysis for degradation of two analogs in plasma.
Figure 3B:
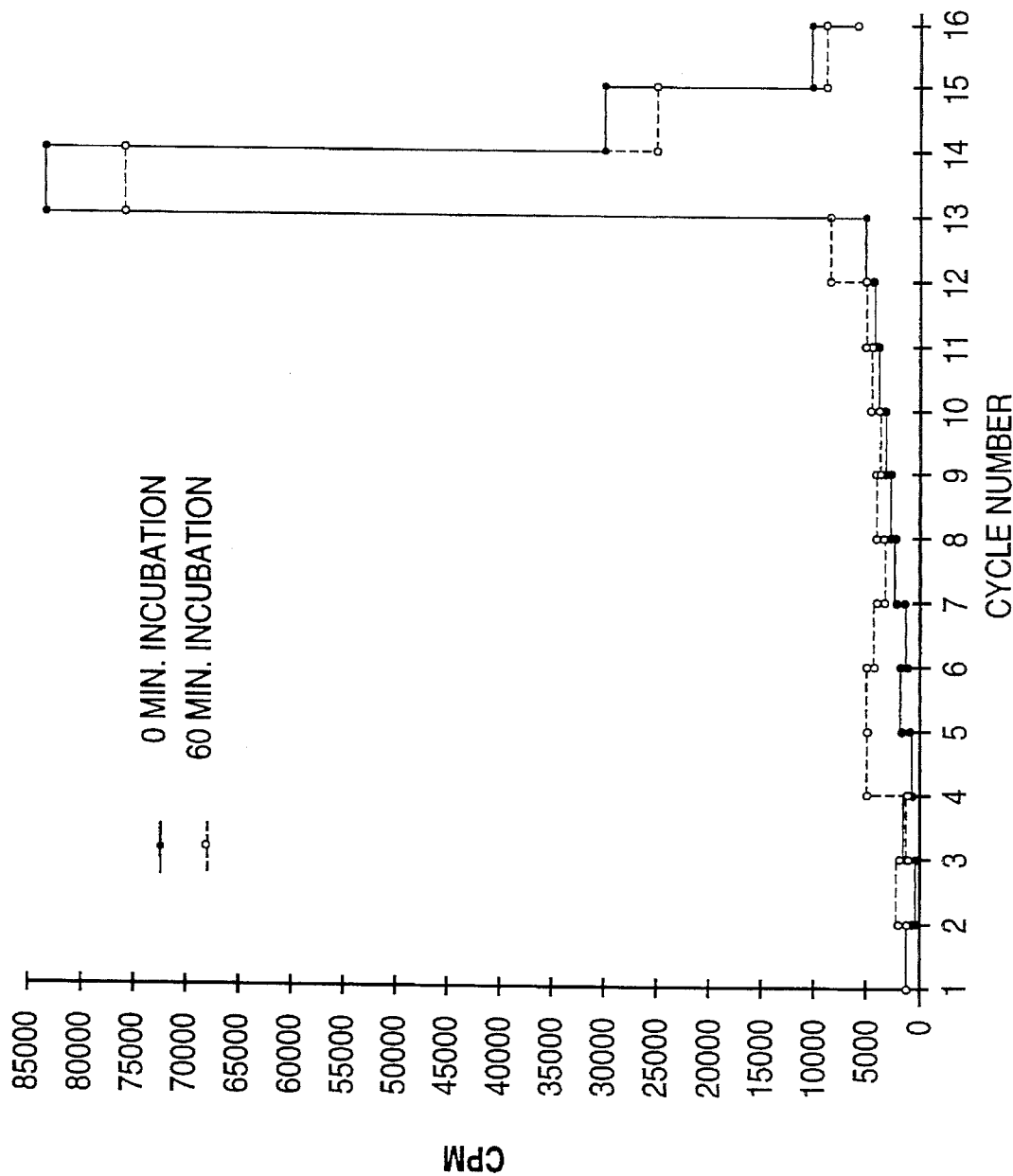

The radiolabel sequencing method of degradation analysis was conducted using a GLP-1(7-37) analog which contained either D-Asp in the 9-position or D-Ala in the 8-position. The results of this assay are shown in FIG. 3. FIG. 3A shows the results for $(D^+)^9$-GLP-1(7-37) and FIG. 3B shows the results for $(A^+)^8$-GLP-1(7-37). As shown in these figures, the $(D^+)^9$ analog degrades in a manner similar to GLP-1(7-37); on the other hand, the $(A^+)^8$ analog showed almost no degradation after 60 minutes.

C. Analogs Tested by RIA

Figure 4:
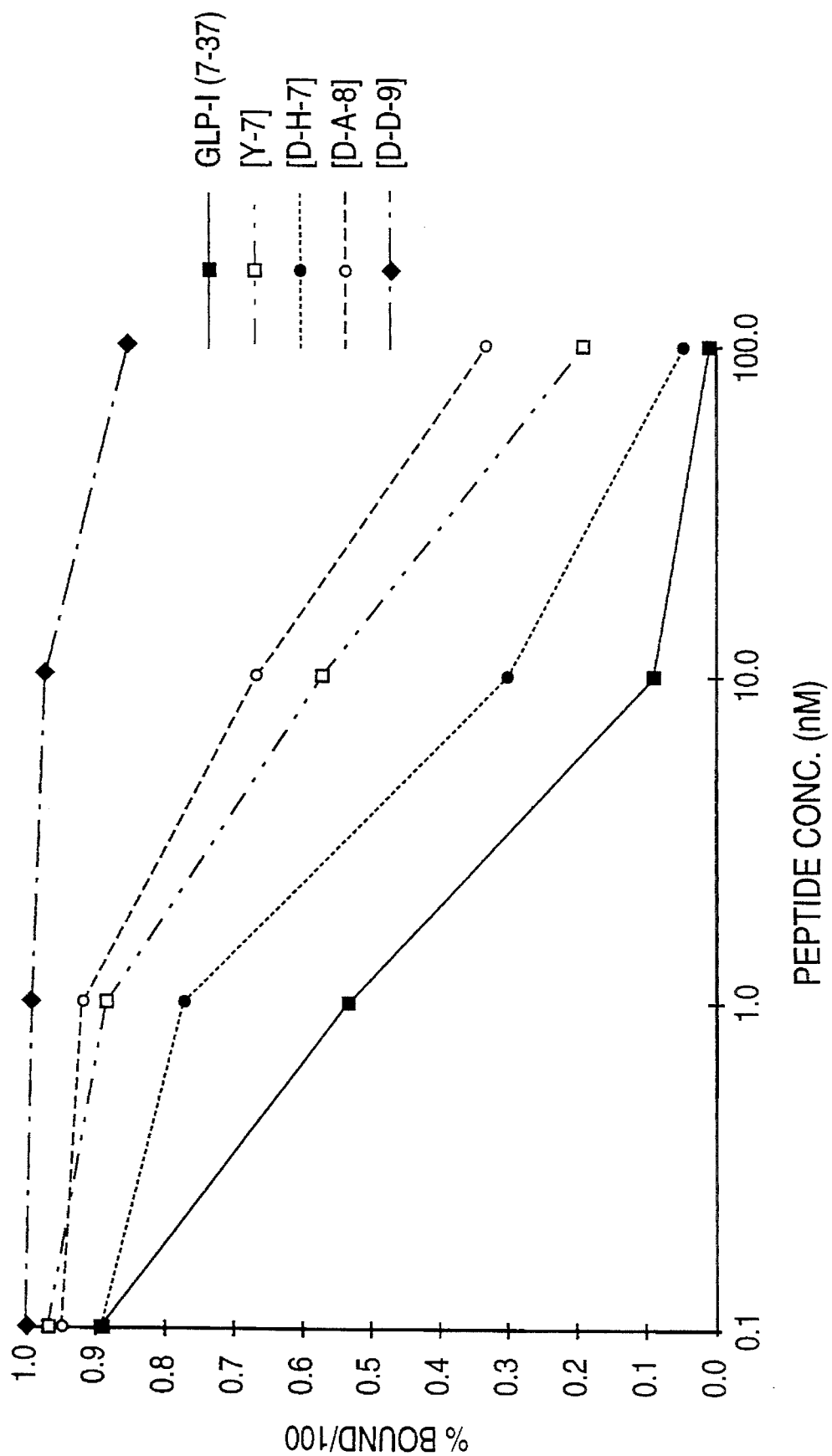
FIG. 4 shows the results of various GLP-1(7-37) analogs with changes in the amino terminal region, to displace $^{125}$I-GLP-1(7-39) from amino terminal specific antiserum.

The N-terminal specific antibody can be used to measure the degradation of analogs only if it is able to cross-react with these analogs, which themselves contain alterations in the N-terminus. FIG. 4 shows the results for analogs modified at positions 7, 8 and 9. $(Y)^7$, $(H^+)^7$ and $(A^+)^8$ appear to be capable although at high concentrations, of cross-reactivity; $(D^+)^9$ is not. The cross-reacting peptides were incubated with plasma for 60 minutes at high concentrations (10–100 nM) and tested by RIA using RIA against the N-terminal specific antibody. Consistent with the results in paragraph B, the $(A^+)^8$ analog was not degraded after 60 minutes, nor was the $(H^+)^7$ analog. However, the $(Y)^7$ analog was degraded.

D. Analogs Shown Protease Resistant by HPLC

The resistance of various analogs to degradation as compared to GLP-1(7-37) was also tested by HPLC as described above. The incubation in plasma was for 60 minutes; either degradation was not observed or was complete after this time. The results are shown in Table 2.

TABLE 2

| Analog | Resistance to Degradation |
|---|---|
| $(H^+)^7$ GLP-1 (7-37) | + |
| (N-acetyl-H)$^7$ GLP-1 (7-37) | + |
| (N-isopropyl-H)$^7$ GLP-1 (7-37) | + |
| $(Y)^7$ GLP-1 (7-37) | − |
| $(K)^7$ GLP-1 (7-37) | − |
| (N-acetyl-K)$^7$ GLP-1 (7-37) | + |
| $(S)^8(Q)^9(Y)^{16}(K)^{18}(D)^{21}$ GLP-1 (7-37) | − |
| $(A^+)^8$ GLP-1 (7-37) | + |
| $(D^+)^9$ GLP-1 (7-37) | − |
| $(E^+)^9$ GLP-1 (7-37) | − |
| $(Q)^9$ GLP-1 (7-37) | − |

We claim:

1. A peptide which is more potent than glucagon in stimulating insulin release from islet cells, said peptide consisting of labeled or unlabeled GLP-1(7-34), GLP-1(7-35), GLP-1(7-36), or GLP-1(7-37) or the C-terminal amide form thereof, having at least one modification selected from the group consisting of:

(a) substitution of a neutral amino acid, arginine, or a D form of lysine for lysine at position 26 and/or 34 and/or a neutral amino acid, lysine, or a D form of arginine for arginine at position 36;

(b) substitution of an oxidation-resistant amino acid for tryptophan at position (c) substitution according to at least one of:
  Y for V at position 16;
  K for S at position 18;
  D for E at position 21;
  S for G at position 22;
  R for Q at position 23;
  R for A at position 24; and
  Q for K at position 26;

(d) a substitution consisting of at least one of:
  an alternative small neutral amino acid for A at position 8;
  an alternative acidic amino acid or neutral amino acid for E at position 9;
  an alternative neutral amino acid for G at position 10; and
  an alternative acidic amino acid for D at position 15; and (e) substitution of an alternative neutral amino acid or the D or N-acylated or alkylated form of histidine for histidine at position 7 wherein for (a), (b), (d) and (e), the substituted amino acids can optionally be in the D form and the amino acids substituted at position 7 can optionally be in the N-acylated or N-alkylated form.

2. The peptide of claim 1 wherein the only modification is as set forth in paragraph (a) of claim 1 and wherein the amino acid substituted for lysine at positions 26 and/or 34 is selected from the group consisting of $K^+$, G, S, A, L, I, Q, M, R and $R^+$ and the amino acid substituted for arginine at position 36 is selected from the group consisting of K, $K^+$ G, S, A, L, I, Q, M, and $R^+$, optionally in combination with a modification as set forth in paragraph (b), (c), (d) or (e) of claim 1.

3. The peptide of claim 1 wherein the only modification is as set forth in paragraph (b) of claim 1 and wherein the amino acid substituted for tryptophan at position 31 is selected from the group consisting of F, V, L, I, A and Y, optionally in combination with a modification as set forth in paragraph (a), (c), (d) or (e) of claim 1.

4. The peptide of claim 1 wherein the only modification is as set forth in paragraph (c) of claim 1 and wherein combined substitutions of S for G at position 22, K at positions 23 and 24 for Q and A, respectively, and Q for K at position 26 have been made, or substitutions of Y for V at position 16 and K for S at position 18 have been made, or these substitutions plus D for E at positions 21 have been made, optionally in combination with a modification as set forth in paragraph (a), (b), (d) or (e) of claim 1.

5. The peptide of claim 1 wherein the only modification is as set forth in paragraph (d) of claim 1 and wherein the small neutral amino acid substituted for alanine at position 8 is selected from the group consisting of S, $S^\dagger$, G, C, $C^\dagger$, Sar, $A^\dagger$, beta-ala, and Aib and the acidic or neutral amino acid substituted for glutamic acid at position 9 is selected from the group consisting of $E^\dagger$, D, $D^\dagger$, Cya, T, $T^\dagger$, N, $N^\dagger$, Q, $Q^\dagger$, Cit, MSO, and acetyl-K, and the alternative neutral amino acid substituted for glycine at position 10 is selected from the group consisting of S, $S^\dagger$, Y, $Y^\dagger$, T, $T^\dagger$, N, $N^\dagger$, Q, $Q^\dagger$, Cit, MSO, acetyl-K, F, and $F^\dagger$, optionally in combination with a modification as set forth in paragraph (a), (b), (c) or (e) of claim 1.

6. The peptide of claim 1 wherein the only modification is as set forth in paragraph (e) of claim 1 and wherein the amino acid substituted for histidine at position 7 is selected from the group consisting of $H^\dagger$, Y, $Y^\dagger$, F, $F^\dagger$, R, $R^\dagger$, Orn, $Orn^\dagger$, M, $M^\dagger$, N-formyl-H, N-formyl-$H^\dagger$, N-acetyl-H, N-acetyl-$H^\dagger$, N-isopropyl-H, N-isopropyl-$H^\dagger$, N-acetyl-K, N-acetyl-$K^\dagger$, P, and $P^\dagger$, optionally in combination with a modification as set forth in paragraph (a), (b), (c), or (d) of claim 1.

7. The peptide of claim 1 which is selected from the group consisting of $(H^\dagger)^7$-GLP-1(7-37), $(Y)^7$-GLP-1(7-37), (N-acetyl-H)$^7$-GLP-1(7-37), (N-isopropyl-H)$^7$-GLP-1(7-37), $(A^\dagger)^8$-GLP-1(7-37), $(E^\dagger)^9$-GLP-1(7-37), $(D)^9$-GLP-1(7-37), $(D^\dagger)^9$-GLP-1(7-37), $(F^\dagger)^{10}$-GLP-1(7-37), $(S)^{22}(R)^{23}(R)^{24}(Q)^{26}$-GLP-1 (7-37), and $(S)^8(Q)^9(Y)^{16}(K)^{18}(D)^{21}$-GLP-1(7-37).

8. A peptide useful to release insulin from islet cells, said peptide having enhanced resistance to degradation in plasma as compared to GLP-1(7-37) and said peptide consisting of labeled or unlabeled GLP-1(7-34), GLP-1(7-35), GLP-1(7-36), or GLP-1(7-37) or the C-terminal amide form thereof, having at least one modification selected from the group consisting of:

(a) substitution of the D form of a neutral or acidic amino acid or the D form of histidine for histidine at position 7;

(b) substitution of a D form of an amino acid for alanine at position 8; and (c) substitution of an N-acylated (1-6C) or N-alkylated (1-6C) form of an alternate amino acid or of histidine for histidine at position 7.

9. The peptide of claim 8 wherein the only modification is as set forth in paragraph (a) of claim 8 and wherein the D form of the amino acid substituted for histidine at position 7 is selected from the group consisting of $P^\dagger$, $D^\dagger$, $E^\dagger$, $N^\dagger$, $Q^\dagger$, $L^\dagger$, $V^\dagger$, $I^\dagger$, and $H^\dagger$, optionally in combination with a modification as set forth in paragraph (b) or (c) of claim 8.

10. The peptide of claim 8 wherein the only modification is as set forth in paragraph (b) of claim 8 and wherein the D-amino acid at position 8 is selected from the group consisting of $P^\dagger$, $V^\dagger$, $L^\dagger$, $I^\dagger$, and $A^\dagger$, optionally in combination with a modification as set forth in paragraph of claim 8.

11. The peptide of claim 8 wherein the only modification is as set forth in paragraph (c) of claim 8 and wherein the alkylated or acetylated amino acid is selected from the group consisting of P, D, E, N, Q, V, L, I, K and H, optionally in combination with a modification as set forth in paragraph (a) or (b) of claim 8.

12. A pharmaceutical composition useful in the treatment of diabetes Type II which comprises an effective amount of the peptide of claim 1 or 8 in admixture with a pharmaceutically acceptable excipient.

13. The peptide of claim 8 which is selected from the group consisting of $(H^\dagger)^7$-GLP-1(7-37), (N-acetyl-H)$^7$-GLP-1(7-37), (N-isopropyl-H)$^7$-GLP-1(7-37), (N-acetyl-K)$^7$-GLP-1(7-37), and $(A^\dagger)^8$-GLP-1(7-37).

14. A peptide which is more potent than glucagon in stimulating insulin release from islet cells, and said peptide consisting of labeled or unlabeled analogs of truncated forms of GLP-1, which consist of GLP-1(7-34), GLP-1(7-35), GLP-1(7-36), or GLP-1(7-37) or the C-terminal amide form thereof, wherein the analog is selected from the group consisting of:

$(H^\dagger)^7$-GLP-1(7-37)

$(Y)^7$GLP-1(7-37), (N-acetyl-H)$^7$-GLP-1(7-37), (N-isopropyl-H)$^7$-GLP-1(7-37), $(A^\dagger)^8$-GLP-1(7-37), $(E^\dagger)^9$-GLP-1(7-37), $(D)^9$-GLP-1(7-37), $(D^\dagger)^9$-GLP-1(7-37), $(F^\dagger)^{10}$-GLP-1(7-37), $(S)^{22}(R)^{23}(R)^{24}(Q)^{26}$-GLP-1(7-37), and $(S)^8(Q)^9(Y)^{16}(K)^{18}(D)^{21}$-GLP-1(7-37).

\* \* \* \* \*